United States Patent [19]

Flemming

[11] Patent Number: 5,316,028
[45] Date of Patent: May 31, 1994

[54] DENTAL FLOSS AND A DEVICE FOR DISPENSING

[76] Inventor: Patricia S. Flemming, 156 Taconic Rd., Greenwich, Conn. 06831

[21] Appl. No.: 80,530

[22] Filed: Jun. 24, 1993

[51] Int. Cl.$^5$ ............................................. A61C 15/00
[52] U.S. Cl. ..................................... 132/329; 132/321
[58] Field of Search ............................... 132/321, 329

[56] References Cited

U.S. PATENT DOCUMENTS

| | | | |
|---|---|---|---|
| 3,837,351 | 9/1974 | Thornton | 132/321 |
| 3,896,824 | 7/1975 | Thornton | 132/321 |
| 4,142,538 | 3/1979 | Thornton | 132/321 |
| 5,159,943 | 11/1992 | Richards et al. | 132/321 |

*Primary Examiner*—Gene Mancene
*Assistant Examiner*—Frank A. LaViola

[57] ABSTRACT

Dental floss is used by almost everyone and recommended by all dentists and professional dental organizations, to preserve and protect the health and the longevity of teeth. The dental floss of the present invention consists of an elongated strand having two or more sections of varying thicknesses and of a continuous length, said varying thickness repeating themselves in many multiples and said multiples being pre-marked for cutting for use. The packaging for the floss of the present invention permits said continuous length of varying thicknesses to be marked for cutting and use at a predetermined length so that the predetermined length contains floss of varying diameters in the central portion thereof and normal floss thickness at either end.

6 Claims, 2 Drawing Sheets

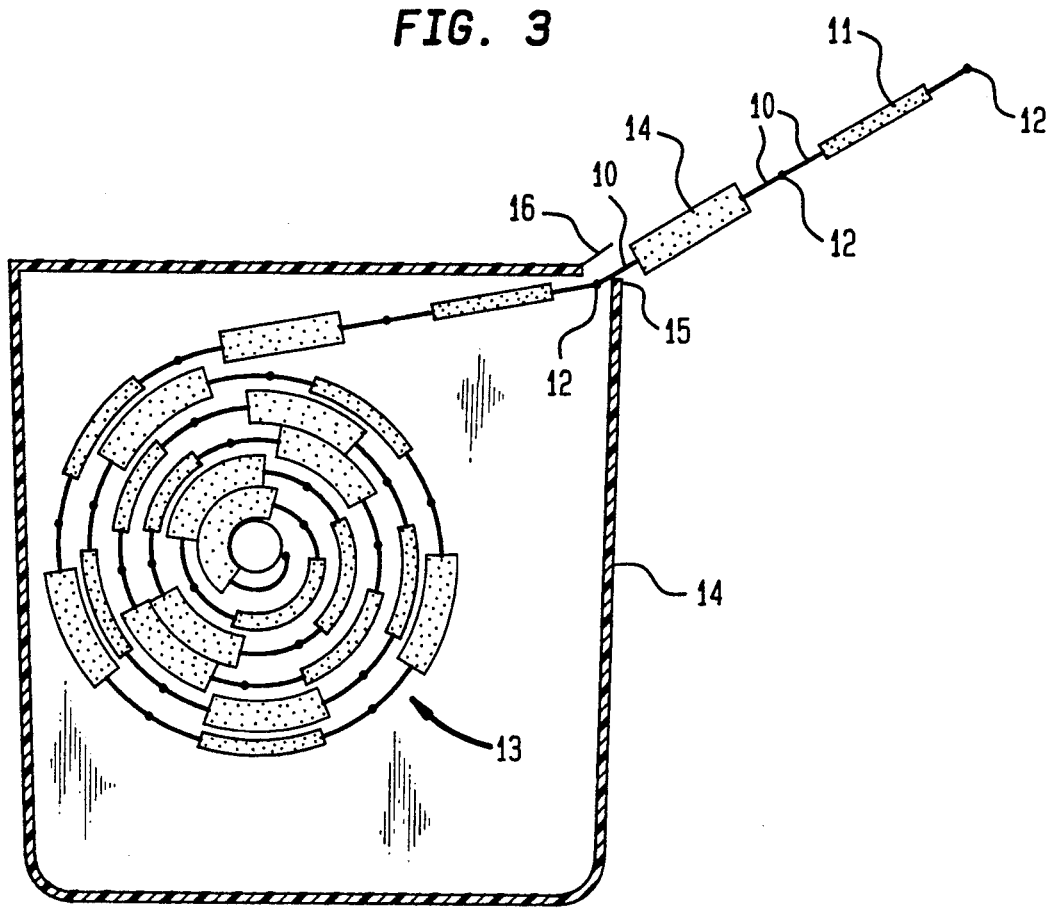

DENTAL FLOSS AND A DEVICE FOR DISPENSING

TECHNICAL FIELD

The present invention relates to dental hygiene and specifically to dental floss and the means for dispensing same.

BACKGROUND OF THE ART

In dental hygiene, it has been found desirable to remove particles of food that may be trapped in the crevices between adjacent teeth. It is well known to use a length of string, commonly called dental floss, to physically remove these particles by passing the string through the crevices of the teeth. The original or normal floss is essentially of a small thin constant diameter. As such, it has been found that this type of floss, that is supplied in a package and is of long continuous length and is cut off by the user at whatever length he may desire, is not capable of filling the larger crevices between teeth that occur naturally in some people and also when there are dentures involved. Thus, while the floss removes some of the particles, there is no assurance that it will essentially and completely fill and clean all of the crevices found in all teeth, to physically remove all the particles in the crevices and rub against and abrase the surface of the teeth defining all the cavities between the teeth.

The following art has been found to be related to the field of the present invention but in no way do any of the herein cited references anticipates or even suggest the novel advance in the field that the present invention makes.

U.S. Pat. No. 3,837,351 issued to Thornton on Sep. 24, 1974 entitled Interdental Tooth Cleaner and Method for Making Same discloses a continuous length of interdental tooth cleaner consisting of textured yarn that is composed of deformed filaments that are covered with a hardened resin to stiffen them and in which the yarn is processed to increase its normal bulkiness. This is not related to the present invention.

U.S. Pat. No. 3,896,824 issued to Thornton on Jul. 29, 1975 entitled Teeth Cleaning discloses a teeth cleaning floss that is to be passed through a crevice between adjacent teeth for dislodging particles therein consisting of a plurality of elongated filaments having a string portion at on end in which the filaments are parallel and closely packed and a spongy brush portion of larger diameter caused by the textured filaments being randomly distorted. There is nothing in this disclosure to teach the novel floss of the present invention, where there is herein disclosed a floss that has one or more different and larger diameter randomly distorted textured filaments with normal size floss filaments at either end of said larger diameter, said combination being repeated in a continuous length of filaments which is pre-marked for cutting and said continuous length being provided in a small firm-boxed package with means for cutting said pre-marked floss for individual use and allowing the remainder of the floss segments to remain clean and in order.

U.S. Pat. No. 4,008,727 issued to Thornton on Feb. 22, 1977 entitled Interproximal Space Tooth Cleaner discloses a variable diameter tooth cleaner formed by a plurality of elongated filaments to have a brush portion and a string portion with the string portion having two parts and with the brush portion being placed between the two parts. There is no teaching of a pre-marked continuous length of alternating normal filaments and one or more larger diameter textured filaments that are pre-marked and packaged for cutting and individual use.

U.S. Pat. No. 4,142,538 issued to Thornton on Mar. 6, 1979 entitled Different Stiffness Continuous Length Teeth Cleaner discloses a continuous length of interproximal space tooth cleaner consisting of textured yarn that is composed of deformed filaments through its complete length with a hardened covering being applied on selected extents thereof without applying an elongating force to the extents. There is no disclosure of alternating normal filaments and textured filaments of one or more greater diameters that are pre-marked for cutting and individual use. U.S. Pat. No. 4,277,297 issued to Thornton on Jul. 7, 1981 entitled Method of Forming Dental Floss with String and Brush Portions discloses only a method of preparing floss with alternating string and brush of continuous length, as does U.S. Pat. Nos. 4,142,538; 3,896,824 and 3,837,351. The present invention does not relate to the method of making the floss; it may be manufactured by any of the above or any other process. The present invention is for a continuous filament length with alternating filament string and one or more filament of greater diameter that is pre-marked and structurally packaged to insure cleanliness, order and pre-marking for cutting and individual use.

OBJECTS OF THE PRESENT INVENTION

It is the object of the present invention to provide a dental floss of alternating normal filament and one or more brush portions of greater diameter in a continuous length.

Another object of the present invention is to provide the dental floss as described above that is pre-marked for cutting and for individual use.

A further object of the present invention to provide a packaging for said continuous length of a dental floss of alternating normal filament and one or more brush portion of greater diameter.

A still further object of the present invention is to provide a pre-marked dental floss that will dislodge particles from between teeth of an individual that has a plurality of different spaces or crevices between their teeth. The present multi-flosses are of only two sizes of cleaners.

Still another object of the present invention is to provide packaging for the pre-marked continuous length alternating dental floss of normal filament and one or more brush portions of greater diameter that allows the individual use to cut a pre-marked length of the floss for use without the problem of the present packaging of two diameter flosses which are all pre-cut and packaged in containers that cause them to become entwined and as one is pulled out for use one or more other flosses come out of the package and fall on the table or on the floor.

DISCLOSURE OF THE INVENTION

These and other objects of the present invention are accomplished by providing a dental floss that is of continuous length and comprises alternate sections of filaments of normal diameter and one or more spongy brush portions of deformed filaments of greater diameter, said floss is pre-marked at a point in the center of said normal filament for cutting for individual use. The brush portions are formed of a plurality of textured, commingled filaments that have been permanently deformed and crinkled to provide a more effective brushing portion. The marked point for cutting is in the form of a bright mark to indicate where the cutting should take place. A special packaging is provided in the present invention that allows the continuous length of the alternating floss of the present invention to be wound around a core in a small pocket size package and led out an exit means. At said exit means, a cutting means is provided with a cutting means that will allow the user to cut the floss at the pre-marked point. The cutting means may be of any workable type such as small knife, a spring loaded cutter or the like.

There are many people who have more than one size of space between their teeth. All of the multi size flosses presently available to the general public are of only two sizes, the normal dental floss filament size and the single size of brush portion of the floss whether it is of the straight line pre-cut type or the also pre-cut loop type. If a person has varying size crevices between his teeth, the presently available multi(two) size flosses may or may not remove all the particles.

This type of problem is over come by the multi-floss of the present invention which contemplates a floss that has the normal size floss filament at each end of each segment of the continuous length floss of the present invention, with one or more of different and greater diameter brushes in between, thereby allowing the individual to cure the problem.

Various other objects, advantages and features of the present invention will become apparent to those skilled in the art from the following discussions, taken in conjunction with the accompanying drawings, which constitute part hereof, wherein:

BRIEF DESCRIPTION OF THE DRAWINGS

FIG. 3 is a plan view of the package for the dental floss of the present invention.

DESCRIPTION OF THE PREFERRED EMBODIMENTS OF THE PRESENT INVENTION

The following is a discussion and description of the preferred specific embodiments of the continuous length dental floss with alternating normal filaments at either end of each segment and one or more spongy brush textured filaments in between of the present invention, such being made with reference to the drawings, whereupon like reference numbers are used to indicate the same or similar parts and/or structure. It is to be understood that such discussion and description is not to unduly limit the scope of the present invention.

Figure 1:
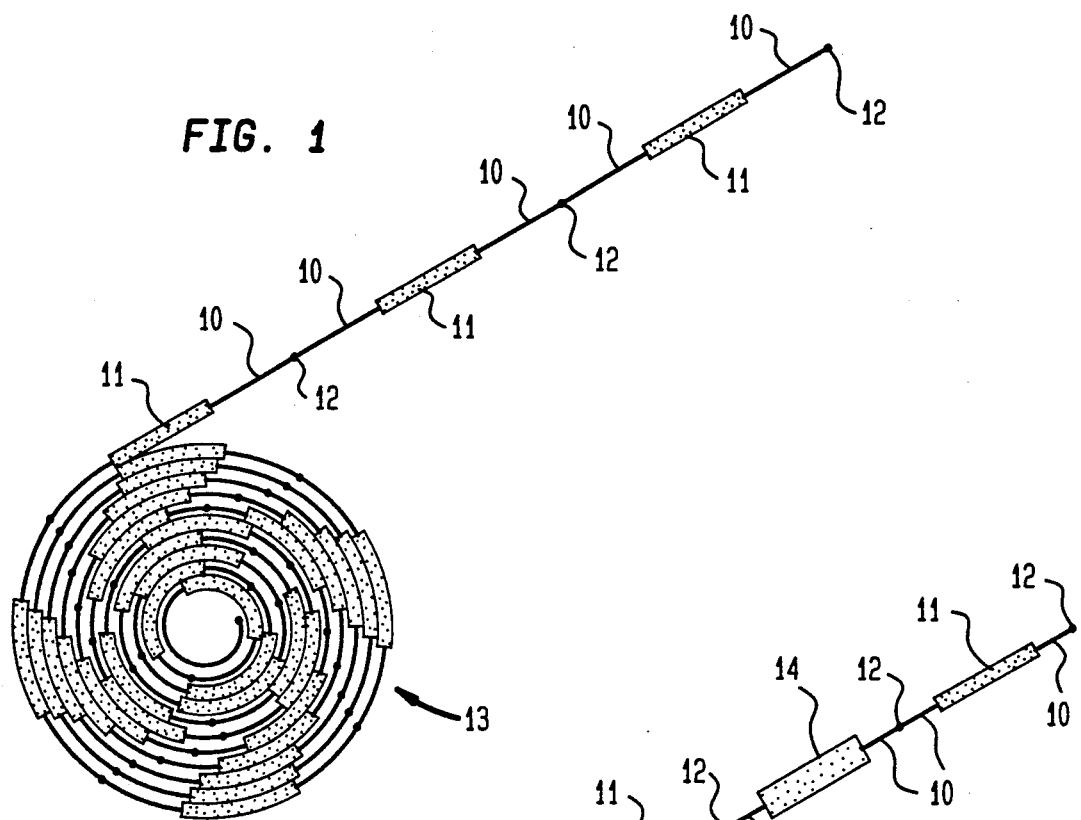
FIG. 1 is a view of dental floss of the present invention, wherein the brush portion is of a single greater diameter than the normal floss filament.
Figure 2:
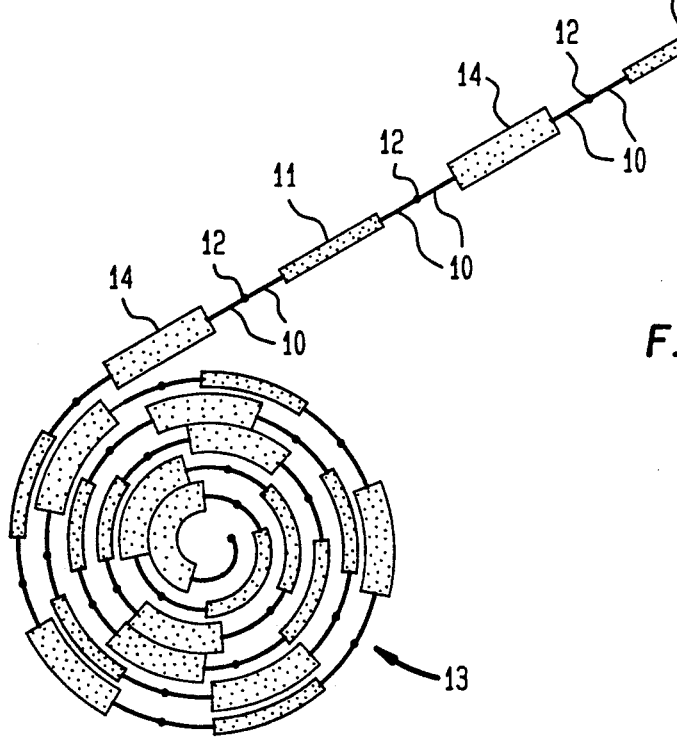
FIG. 2 is a view of the dental floss of the present invention, wherein the brush portion is of two different greater diameter than the normal floss filament.

Referring now to the drawings, the dental floss of the present invention is shown in FIGS. 1 and 2 with a single brush in FIG. 1 and a two different greater diameter brush in FIG. 2, wherein the normal diameter floss is at 10, the greater diameter textured filament is at 11, the pre-marked cutting location for individual use is at 12 and a storage or delivery spool at 13. FIG. 2 shows the larger textured brush filament is at 14.

FIG. 3 shows the unique pocket packaging of the present invention wherein the case is at 17 the storage or delivery spool is 13, the cutting edge is at 15 and the exit opening is at 16.

From the foregoing, it can readily be seen that the present invention provides a greatly improved dental floss and packaging for same. In view to the foregoing description, the principles of the present invention can readily be extended by those skilled in the art of dental floss, designers, manufactures and packagers, other than those specifically disclosed herein. Thus, although the present invention has been described with reference to particular preferred embodiments thereof, many changes and modifications will become readily apparent to those skilled in the art in view of the foregoing description which is intended to be illustrative and not limiting of the present invention as defined by the appended claims.

What is claimed is:

1. An interdental tooth cleaner comprising:
    a continuous elongated flexible string of filaments having a continuous length, said elongated string of filaments having a first brush portion and a string portion, said first brush portion having as diameter greater than the diameter of the string portion, and a second brush portion having a diameter greater than each of said first brush portion and said string portion, said first brush portion, second brush portion and said string portion forming a repeating pattern along the continuous length of the elongated flexible string of filaments;
    said first and second brush portions being formed of a plurality of textured, commingled filaments that have been permanently deformed and crinkled and the string portion being formed of a plurality of essentially straight filaments that are unitary with textured, commingled filaments of the brush portions; and
    a bright mark for cutting being formed on the string portion, said bright mark repeating along the continuous length of the elongated flexible string of filaments and being located at a same portion of said repeating pattern.

2. The interdental tooth cleaner of claim 1, wherein additional brush portions of larger diameter than the second brush portion are formed along the continuous length of said string of filaments thereby creating a different repeating pattern.

3. The interproximal tooth cleaner of claim 1, wherein said repeating bright mark for cutting is placed generally in the center of said string portion, said string portions being of sufficient length to enable a user, when said repeating pattern is cut, to grasp each opposite string portion end for use.

4. The interdental tooth cleaner of claim 3, wherein said continuous elongated string of filaments is provided with an enclosed packet capable of being carried in a pocket, said continuous elongated string of filaments being wrapped around a core and leads to an exit means, and a cutting means being provided at said exit means to cut each repeating pattern at said bright mark.

5. The interdental tooth cleaner of claim 4, wherein said cutting means is a knife.

6. The interdental tooth cleaner of claim 4, wherein said cutting means is spring loaded and is closeable.

* * * * *